(12) United States Patent
Dar et al.

(10) Patent No.: US 7,632,239 B2
(45) Date of Patent: Dec. 15, 2009

(54) SENSOR DEVICE FOR GAIT ENHANCEMENT

(75) Inventors: Amit Dar, Kefar-Hess (IL); Jonathan Bar-Or, Pardes Hanna (IL)

(73) Assignee: Bioness Neuromodulation Ltd., Raanana (IL)

( * ) Notice: Subject to any disclaimer, the term of this patent is extended or adjusted under 35 U.S.C. 154(b) by 0 days.

(21) Appl. No.: 11/552,997

(22) Filed: Oct. 26, 2006

(65) Prior Publication Data
US 2007/0112285 A1     May 17, 2007

Related U.S. Application Data

(60) Provisional application No. 60/736,858, filed on Nov. 16, 2005, provisional application No. 60/746,060, filed on May 1, 2006, provisional application No. 60/805,359, filed on Jun. 21, 2006.

(51) Int. Cl.
A61B 5/103     (2006.01)
(52) U.S. Cl. .................. 600/592; 600/595; 600/587
(58) Field of Classification Search ................ 600/592, 600/595
See application file for complete search history.

(56) References Cited

U.S. PATENT DOCUMENTS

| | | | |
|---|---|---|---|
| 3,204,637 A | | 9/1965 | Frank et al. |
| 4,580,569 A | | 4/1986 | Petrofsky |
| 4,647,918 A | * | 3/1987 | Goforth ................... 340/573.1 |
| 5,167,229 A | | 12/1992 | Peckham et al. |
| 5,253,654 A | * | 10/1993 | Thomas et al. .............. 600/592 |
| 5,323,650 A | * | 6/1994 | Fullen et al. .................. 73/172 |
| 5,330,516 A | | 7/1994 | Nathan |
| 5,350,414 A | | 9/1994 | Kolen |
| 5,357,696 A | * | 10/1994 | Gray et al. ..................... 36/136 |
| 5,408,873 A | * | 4/1995 | Schmidt et al. ........ 73/862.625 |
| 5,487,759 A | | 1/1996 | Bastyr et al. |
| 5,540,735 A | | 7/1996 | Wingrove |
| 5,562,707 A | | 10/1996 | Prochazka et al. |
| 5,643,332 A | | 7/1997 | Stein |
| 5,664,346 A | * | 9/1997 | Barker .......................... 36/137 |
| 5,748,845 A | | 5/1998 | Labun et al. |
| 5,775,332 A | * | 7/1998 | Goldman .................... 600/587 |
| 5,814,093 A | | 9/1998 | Stein |

(Continued)

OTHER PUBLICATIONS

Non-Final Office Action for U.S. Appl. No. 11/380,430 mailed Mar. 5, 2009.

(Continued)

*Primary Examiner*—Max Hindenburg
*Assistant Examiner*—Michael C Stout (57) ABSTRACT

A foot sensor device and method for gait enhancement, the device including: (a) a sensor unit having a casing, the sensor unit for disposing within a shoe of a user, the sensor unit for sensing a parameter associated with a gait event; (b) an electronic communication unit, electrically associated with the sensor unit, for receiving a signal pertaining to the parameter, the electronic unit having,: (i) a microcontroller; (ii) a transmitting unit for transmitting, in a wireless fashion, gait information based on the signal, to a unit of an orthosis external to the foot sensor device, and (iii) a housing for housing at least one of the microcontroller and the transmitting unit, and (c) a fastening unit, attached to the housing, adapted to fasten on to the shoe, so as to secure the communication unit in a fixed position during gait

24 Claims, 7 Drawing Sheets

U.S. PATENT DOCUMENTS

| | | | |
|---|---|---|---|
| 5,980,472 A | 11/1999 | Seyl | |
| 6,126,355 A | 10/2000 | Clover, Jr. | |
| 6,174,294 B1 * | 1/2001 | Crabb et al. | 600/592 |
| 6,195,921 B1 * | 3/2001 | Truong | 36/136 |
| 6,246,863 B1 * | 6/2001 | Kampel | 455/100 |
| 6,349,126 B2 * | 2/2002 | Ogawa et al. | 377/24.2 |
| 6,456,884 B1 | 9/2002 | Kenney | |
| 6,456,885 B1 | 9/2002 | Shiba et al. | |
| 6,507,757 B1 * | 1/2003 | Swain et al. | 607/49 |
| 6,516,500 B2 * | 2/2003 | Ogino et al. | 24/504 |
| 6,564,103 B2 | 5/2003 | Fischer et al. | |
| 6,578,745 B1 * | 6/2003 | Taylor et al. | 224/197 |
| D494,273 S * | 8/2004 | Haugland et al. | D24/155 |
| 6,829,510 B2 | 12/2004 | Nathan et al. | |
| 7,146,220 B2 | 12/2006 | Dar et al. | |
| 7,162,305 B2 | 1/2007 | Tong et al. | |
| 7,174,607 B1 * | 2/2007 | Buettell | 24/504 |
| 7,200,517 B2 * | 4/2007 | Darley et al. | 702/160 |
| 7,337,007 B2 | 2/2008 | Nathan et al. | |
| 7,403,821 B2 | 7/2008 | Haugland et al. | |
| 7,410,471 B1 | 8/2008 | Campbell et al. | |
| 7,416,537 B1 | 8/2008 | Stark et al. | |
| 2003/0114892 A1 | 6/2003 | Nathan et al. | |
| 2004/0122483 A1 | 6/2004 | Nathan et al. | |
| 2004/0147975 A1 | 7/2004 | Popovic et al. | |
| 2004/0254624 A1 | 12/2004 | Johnson | |
| 2005/0049652 A1 | 3/2005 | Tong | |
| 2005/0131317 A1 * | 6/2005 | Oddsson et al. | 600/592 |
| 2005/0261609 A1 * | 11/2005 | Collings et al. | 600/592 |
| 2006/0282017 A1 * | 12/2006 | Avni et al. | 600/587 |
| 2006/0282018 A1 * | 12/2006 | Balzano | 600/587 |
| 2007/0021689 A1 * | 1/2007 | Stergiou et al. | 600/595 |
| 2007/0112394 A1 | 5/2007 | Nathan et al. | |
| 2007/0179560 A1 | 8/2007 | Tong et al. | |
| 2008/0140154 A1 | 6/2008 | Loeb et al. | |
| 2009/0069865 A1 | 3/2009 | Lasko et al. | |

OTHER PUBLICATIONS

Strojnik, P., Acimovic, R., Vavken, E., Simic, V. and Stanic, U. (1987) Treatment of drop foot using an implantable peroneal underknee stimulator. Scandanavian J. of Rehabil. Med. 19:37-43.

Kralj, A.R. & Bajd, T. (1989) Functional Electrical Stimulation: Standing and Walking after Spinal Cord Injury, CRC Press, Boca Raton, FL., pp. 1.15.

International Preliminary Report on Patentability for PCT/IL07/00531, mailed Mar. 19, 2009, 5 pages.

International Search Report for PCT/IL07/00531, mailed Jul. 7, 2008, 2 pages.

* cited by examiner

SENSOR DEVICE FOR GAIT ENHANCEMENT

This application draws priority from U.S. Provisional Patent Application Ser. Nos. 60/736,858, filed Nov. 16, 2005, 60/746,060, filed May 1, 2006, and 60/805,359, filed Jun. 21, 2006.

FIELD AND BACKGROUND OF THE INVENTION

The present invention relates to sensor devices for gait enhancement, and more particularly, to such a sensor device having an attachment mechanism for attaching the device to the rim of a shoe.

It is known that various pathologies of the neuromuscular system due to disease or trauma to the central nervous system, such as stroke, spinal cord injury, head injury, cerebral palsy and multiple sclerosis, can impede proper limb functioning of the legs. Gait, the biomechanical description of walking, can suffer static and dynamic parameter variations due to neuromuscular impairments that cause non-symmetrical walking and reduced walking speed and stability, and often require increased energy consumption.

Drop foot describes the gait attributable to weak or uncoordinated activation of the ankle dorsi-flexors due to disease or trauma to the central nervous system A patient suffering from drop foot tends to drag the foot during the swing phase of walking and usually try to compensate for this dragging by hiking the hip or swinging the affected leg in a circular motion. These patients tend to have impaired stability, are prone to frequent falls, and have walking movements that are unaesthetic and energy consuming It is known, however, that functional electrical stimulation (FES) can Generally be used to activate the leg muscles of such patients Precisely timed bursts of short electrical pulses are applied to motor nerves to generate muscle contractions, which are synchronized with the gait of the patient, so as to improve the leg function and enhance the gait Commercially available FES devices utilize a sensor, for disposing underneath the foot of the user, to trigger the electrical pulses being applied to the motor nerves. The sensor senses foot rise or foot strike and accordingly triggers the stimulation pulses administered to the motor nerves. The sensor device is physically distinct from the orthosis.

U.S. Pat. No. 6,507,757 to Swain, et al., discloses one typical foot sensor device of the prior art, in which a foot pressure switch, or sensor, is permanently disposed in the shoe of the affected leg. An electrical circuit is interrupted during the stance phase, when a significant weight is placed on the heel, and reconnects when the heel is lifted during the swing phase. Wires disposed under the clothing connect the sensor with an external stimulator unit that can be attached to the belt or kept in a pocket of the user. The stimulator unit is connected to the electrodes by additional electrical wires In other FES orthotic devices, the cumbersome wires are obviated by using a radio frequency (RF) system in which the foot sensor device and other components of the FES orthotic device communicate in a wireless fashion. However, the use of such an RF system necessitates integrating an RF transmitting unit, or head, within the foot sensor device The transmitting unit can be bulky and sensitive to humidity and mechanical stress. Consequently, such transmitting units are typically mounted on and attached to the calf of the patient.

U.S. Design Pat. No. D494,273 to Haugland, et al., assigned to Neurodan A/S, describes a pressure sensor switch device for placing underneath the foot of the patient. The communication head is held at a predetermined distance from the sensor device by a wide, semi-rigid spine. The device disclosed by Haugland, et al., can be used as a component of the ActiGait® system manufactured by Neurodan A/S. In the ActiGait® system, the pressure sensor device is inserted into a small pouch within a sock, such that upon donning of the sock, the pressure switch is disposed underneath the foot A substantially non-elastic band is tightened around the calf to secure the RF unit in place against the calf of the impaired leg.

This approach is disadvantageous in that the patient, who is often hemiplegic or may suffer from other disorders, is required to add the donning of an additional item—the sock—to his routine This unintuitive action is particularly problematic for patients who need or prefer to don the FES orthotic device in an unassisted fashion.

A further disadvantage of this design is that the semi-rigid spine may rub against the foot and heel Also, the electronic head that houses the RF transceiving unit may rub the ankle or lower calf of the user during the course of gait. Moreover, because the pressure switch and RF transceiving unit are mechanically connected by a wide, at least semi-rigid neck, pressures exerted on the electronic head (e.g., when the head gets caught on, or bumped by, an object during the course of gait), are mechanically translated into forces on the foot sensor. These forces may impede the efficacy and sensitivity of the foot sensor. A further disadvantage lies in the limited ability to adjust the electronic head of the pressure switch to different shoe heights: the electronic head protrudes excessively from low-rimmed shoes, and cannot be fitted to shoes or boots in which the rim is at or above the height of the electronic head.

There is therefore a recognized need for, and it would be highly advantageous to have, a sensor device for neuroprosthetic gait enhancement that overcomes the various deficiencies of the prior art devices. It would be of particular advantage to have such a sensor device that is essentially effortless to don, avoids the discomfort associated with prior art sensor devices, and is secured so as to operate in a safe and robust fashion,

SUMMARY OF THE INVENTION

According to the teachings of the present invention there is provided a foot sensor device for gait enhancement, including: (a) a sensor unit having an external casing, the sensor unit for disposing within a shoe of a user, the sensor unit for sensing, a parameter associated with a gait event; (b) an electronic communication unit, electrically associated with the sensor unit, for receiving a signal pertaining to the parameter, the electronic unit having: (i) a microcontroller; (ii) a transmitting unit for transmitting, in a wireless fashion, gait information based on the signal, to a unit of an orthosis external to the foot sensor device, and (iii) a housing for housing at least one of the microcontroller and the transmitting unit, and (c) a fastening unit, attached to the housing, the fastening unit adapted to fasten on to the shoe, so as to secure the electronic communication unit in a substantially fixed position during gait of the user.

According to further features in the described preferred embodiments, the fastening unit includes a clamp unit.

According to still further features in the described preferred embodiments, the fastening unit is adapted to fasten on to a rim of the shoe.

According to still further features in the described preferred embodiments, the clamp unit has at least two arms designed and configured to fasten around a rim of the shoe.

According to still further features in the described preferred embodiments, the clamp unit is at least semi-rigidly associated with the housing.

According to still further features in the described preferred embodiments, the clamp unit is rigidly associated with the housing.

According to still further features in the described preferred embodiments, the housing of the electronic unit and the external casing of the sensor unit are substantially mechanically independent.

According to still further features in the described preferred embodiments, the clamp unit further includes a locking lever adapted for locking the arms in position around the rim of the shoe.

According to still further features in the described preferred embodiments, a facing of the housing is concave, so as to fit a natural curvature of a leg of the user.

According to still further features in the described preferred embodiments, the housing and the clamp unit each have a face for disposing towards a leg of the user when the user wears the shoe, the device being designed and configured such that the housing and the clamp unit are attached to form an angle within a range of about 150° to about 175° between the faces.

According to still further features in the described preferred embodiments, the angle is in a range of about 155° to about 175°.

According to still further features in the described preferred embodiments, the angle is in a range of about 160° to about 175°.

According to still further features in the described preferred embodiments, the angle is in a range of about 160° to about 170°.

According to still further features in the described preferred embodiments, the transmitting unit is a transceiving unit.

According to still further features in the described preferred embodiments, the device further includes: (d) the shoe.

According to still further features in the described preferred embodiments, the sensor unit is disposed under an inner sole of the shoe.

According to still further features in the described preferred embodiments, the fastening unit includes a clamp unit adapted to enable a hemiplegic patient to affix the clamp unit to the shoe, using a single hand.

According to still further features in the described preferred embodiments, the housing is a casing.

According to another aspect of the present invention there is provided a method of enhancing gait including the steps of: (a) providing a device including: (i) a sensor unit having an external casing, the sensor unit for disposing within a shoe of a user, the sensor unit for sensing a parameter associated with a gait event; (ii) an electronic communication unit, electrically associated with the sensor unit, for receiving a signal pertaining to the parameter, the electronic unit having: (A) a microcontroller; (B) a transmitting unit for transmitting, in a wireless fashion, gait information based on the signal, to a unit of an orthosis external to the foot sensor device, and (C) a housing for housing at least one of the microcontroller and the transmitting unit, and (iii) a fastening unit, attached to the housing, the fastening, unit adapted to fasten on the shoe, so as to secure the electronic communication unit in a substantially fixed position during gait of the user, and (b) donning the device by affixing the fastening unit to the shoe.

According to further features in the described preferred embodiments, the affixing of the fastening unit includes affixing of a clamp unit.

According to still further features in the described preferred embodiments, the fastening unit is affixed to a rim of the shoe.

According to still further features in the described preferred embodiments, the method further includes, prior to step (b), the step of (c) disposing the sensor unit under an inner sole of the shoe.

According to still further features in the described preferred embodiments, the affixing of the fastening unit is effected using a single hand, even by a hemiplegic patient using a single hand.

According to still further features in the described preferred embodiments, the method further includes the step of: (c) locking the arms in position against the rim of the shoe.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 6b is a schematic, three-dimensional top view of FIG. 6a.

DESCRIPTION OF THE PREFERRED EMBODIMENTS

One embodiment of the present invention is a sensor device for neuroprosthetic gait enhancement, the device designed for facile yet secure attachment to the rim of the user's shoe, even by a hemiplegic user.

Before explaining at least one embodiment of the invention in detail, it is to be understood that the invention is not limited in its application to the details of construction and the arrangement of the components set forth in the following description or illustrated in the drawings The invention is capable of other embodiments or of being practiced or carried out in various ways Also, it is to be understood that the phraseology and terminology employed herein is for the purpose of description and should not be regarded as limiting.

Figure 1:
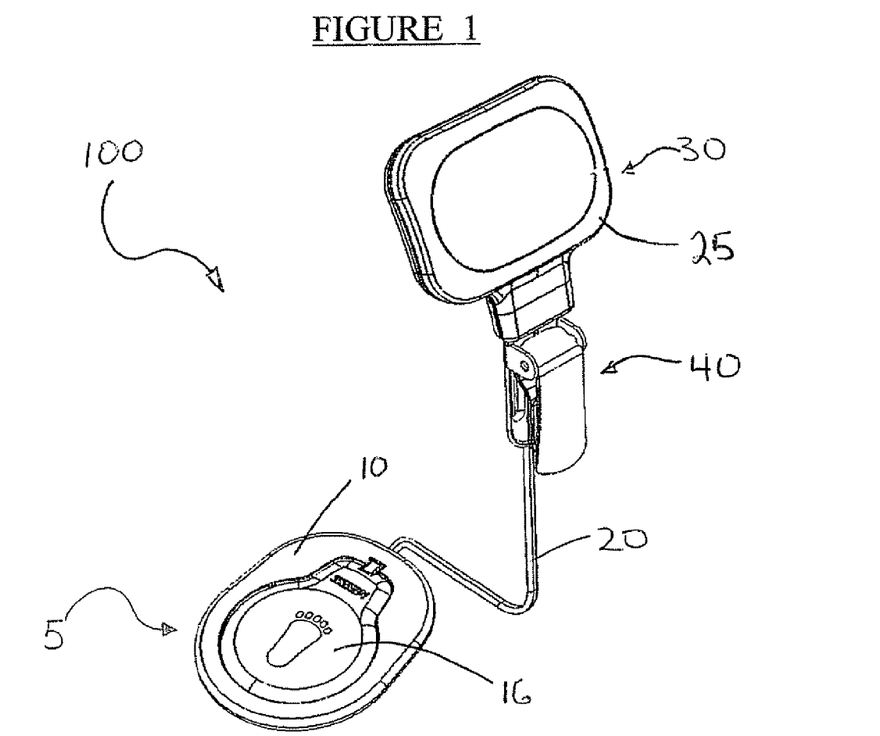
FIG. 1 is a perspective view of the inventive foot sensor device.

Referring now to the drawings, FIG. 1 a perspective view of the inventive foot sensor device 100 for a gait-enhancing orthosis. Foot sensor device 100 includes a sensor unit 5 having a sensor casing 10, in which is disposed a sensor element 16, a communication unit 30 enclosed by housing 25, and wiring (wire or cable) 20 for mechanically and electrically connecting sensor element 16 and communication unit 30. Foot sensor device 100 further includes a fastening unit such as clamp unit 40, rigidly or at least semi-rigidly attached to communication unit 30, for attaching communication unit 30 to the user's shoe, and more typically, to the rim of the user's shoe (see FIG. 2 hereinbelow). It should be stressed that sensor element 16 of inventive foot sensor device 100, in contrast to RF-based foot sensor devices of the prior art, is substantially mechanically independent of communication unit 30. The advantages of this attribute are elaborated hereinbelow.

As used herein in the specification and in the claims section that follows, the term "substantially mechanically independent" refers to two components, electrically and mechanically connected, and physically set apart from one another, the components having substantially no constraint when moved towards one another. A typical example of such substantially mechanically independent components is communication unit 30 and sensor casing 10, connected by a flexible conductive wire.

Figure 2:
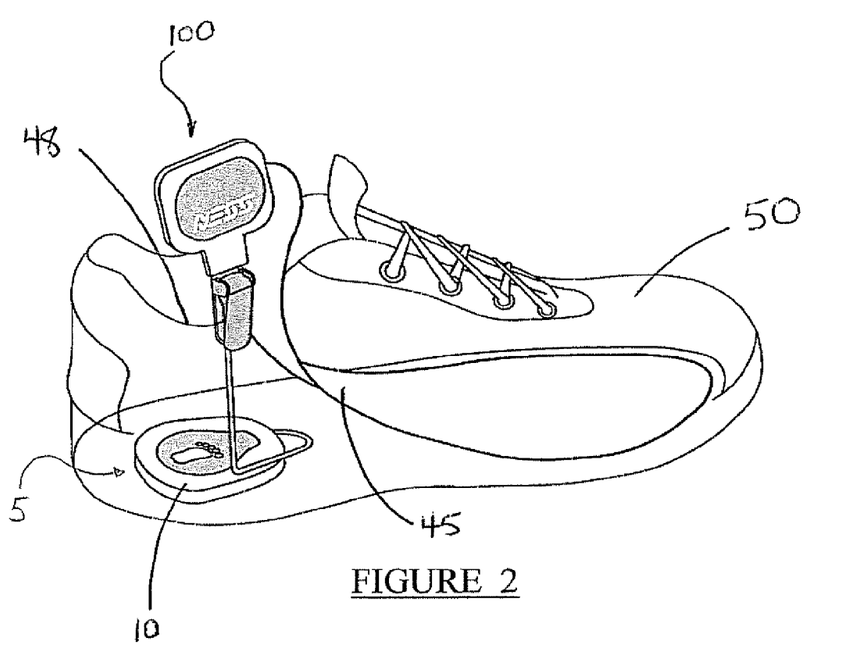
FIG. 2 is a schematic, three-dimensional view of the inventive foot sensor device, the sensor unit being disposed underneath the shoe insole, and the communication unit being mounted on the shoe rim.

Generally in the prior art, the foot pressure switch, or the sensor, is either permanently disposed in the shoe, or disposed in a small pouch of a sock, as in the above-described ActiGait® systems As shown in FIG. 2, by sharp contrast, sensor unit 5 is preferably placed under an inner sole 45 of a shoe 50, beneath the heel area. Sensor casing 10 can be removed or repositioned with facility, by lifting up or removing inner sole 45.

Figure 2A:
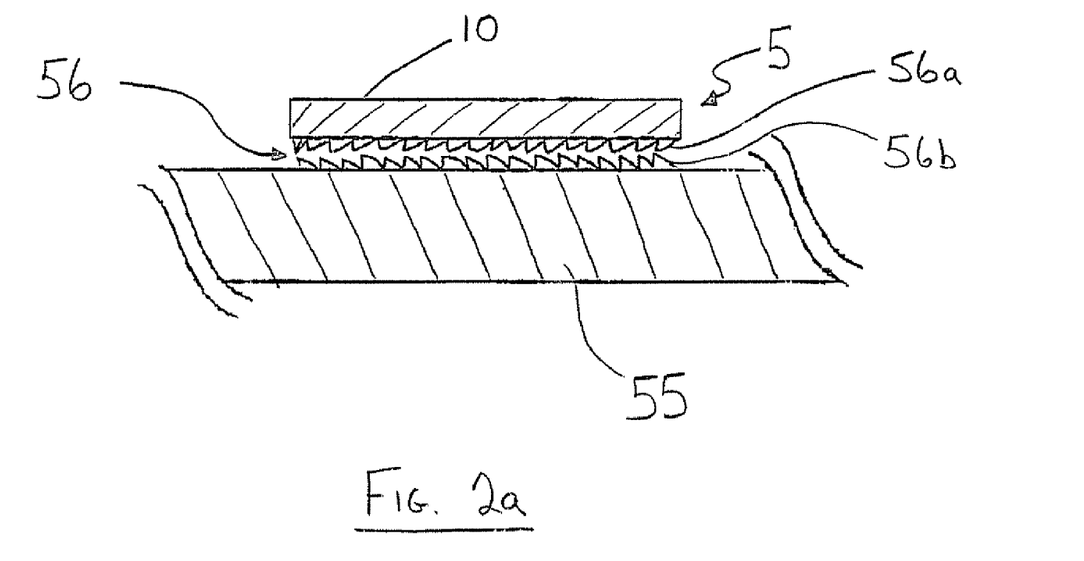
FIG. 2a is a partial cross-sectional view of a shoe floor, a sensor casing, and a hook and loop system for affixing the casing to the floor.

As shown in a cross-sectional view in FIG. 2*a,* sensor unit 5 may advantageously secured to the floor 55 of the shoe by a hook and loop system 56 such as Velcro®. By way of example, hooks 56*a* of hook and loop system 56 may be attached to sensor casing 10, and loops 56*b* may be attached to floor 55. In particular cases, sensor casing 10 may also be positioned under the forefoot area of the shoe.

Casino 10 is configured to protect the inner sensor element against mechanical stress and wetness, and is made of two flexible layers, selected such that the upper layer is more flexible than the lower layer. An additional piece of sponge-like material lies between the internal layer and the sensor, providing additional protection to the sensor. The two layers of sensor casing 10 are attached by various means such as ultrasonic welding, RF welding, gluing, heat welding, or pins. Casing 10 is connected to communication unit 30 by means of wiring 20, which is long enough to enable attachment of communication unit 30 to a rim 48 of shoe 50, irrespective of the height of the shoe rim. It should be noted that when the shoe is not worn, foot sensor device 100 can be left attached to shoe 50, such that the user is not challenged with an additional, cumbersome, and unintuitive doffing action, and in subsequent use, a similarly challenging donning action.

The positioning of communication unit 30 above the rim of shoe 50 protects communication unit 30 from being banged and rubbed by external objects, and from exposure to dirt and moisture Such positioning may also serve to keep communication unit 30 hidden under the trousers, which is aesthetically desirable and, perhaps more importantly, protects communication unit 30 from being caught or bumped during gait.

Moreover, in foot sensor device 100 of the present invention, the height of communication unit 30 on the leg of the user is substantially fixed with the height of the shoe rim. In the above-referenced design patent to Haugland, et al., by sharp contrast, the distance between the communication unit and the sensor unit is determined by the semi-rigid spine connecting therebetween, such that the height of the communication unit is not adjustable. Consequently, the entire communication unit may not extend over the shoe rim in boots and other high-rimmed shoes, and the communication unit may be disposed at a disadvantageously distance from the shoe rim in low shoes.

Another advantage of the foot sensor device 100 of the present invention is that wiring 20 is thin and is easily contained within the shoe. The wide spine of the device disclosed by Haugland, et al., is bulky, such that the user is subject to the distraction of sensing the spine within the shoe, even to the point of experiencing discomfort.

Perhaps most significantly, foot sensor device 100 may be advantageously fixed to the rim of the shoe in a semi-permanent fashion, i e, even during those periods in which the user is not undergoing neuroprosthetic gait enhancement Thus, prior to activating or reactivating the device, no additional donning procedure is required.

Figure 3:
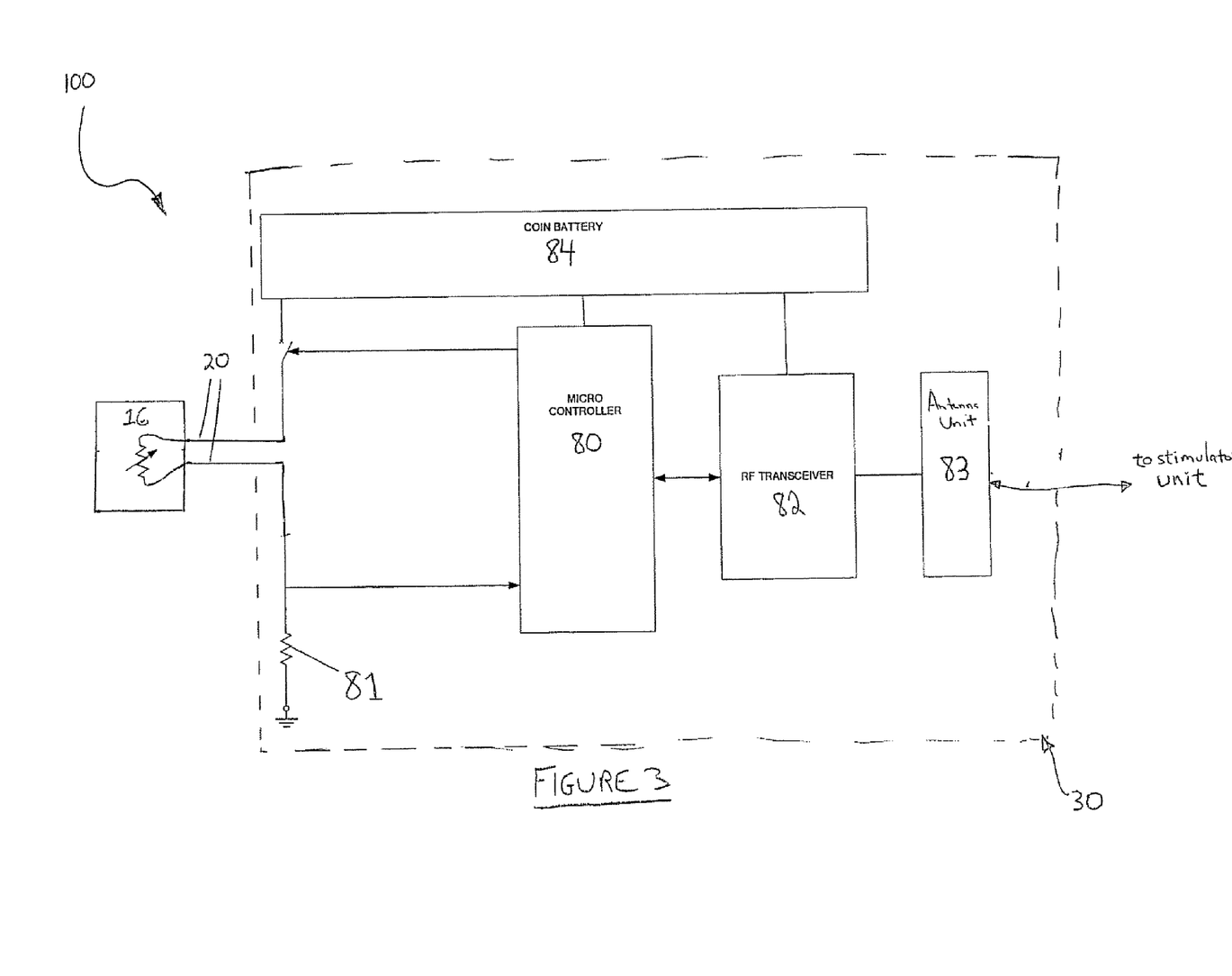
FIG. 3 is a schematic electronic diagram of the inventive foot sensor device.

FIG. 3 is a schematic electronic diagram of inventive foot sensor device 100. Sensor element 16 is connected to, and preferably powered by, electronics or communication unit 30 by means of wiring 20 Communication unit 30 includes a microcontroller 80, a radio frequency (RF) transceiver 82, and an antenna unit 83 having a matching network for converting the signal from the wired medium to a wireless medium, and from the wireless medium to the wired medium.

The resistance of sensor element 16 changes with the force applied thereon. In order to measure the actual resistance of sensor element 16, foot sensor device 100 is equipped with a voltage divider consisting of sensor element 16 and a bias resistor 81 preferably disposed in unit 30. When a voltage is applied to the voltage divider, the voltage is divided according to the resistance ratio between sensor element 16 and bias resistor 81. This voltage is measured in order to assess the resistance of sensor element 16.

Communication unit 30 is also equipped with a small coin battery 84 that provides power to microcontroller 80, RF transceiver 82, and sensor element 16.

Microcontroller 80 controls and monitor the operation of foot sensor device 100 and executes the algorithms thereof Preferably, microcontroller 80 communicates with RF transceiver 82 via a Serial Peripheral Interface (SPI).

Figure 4:
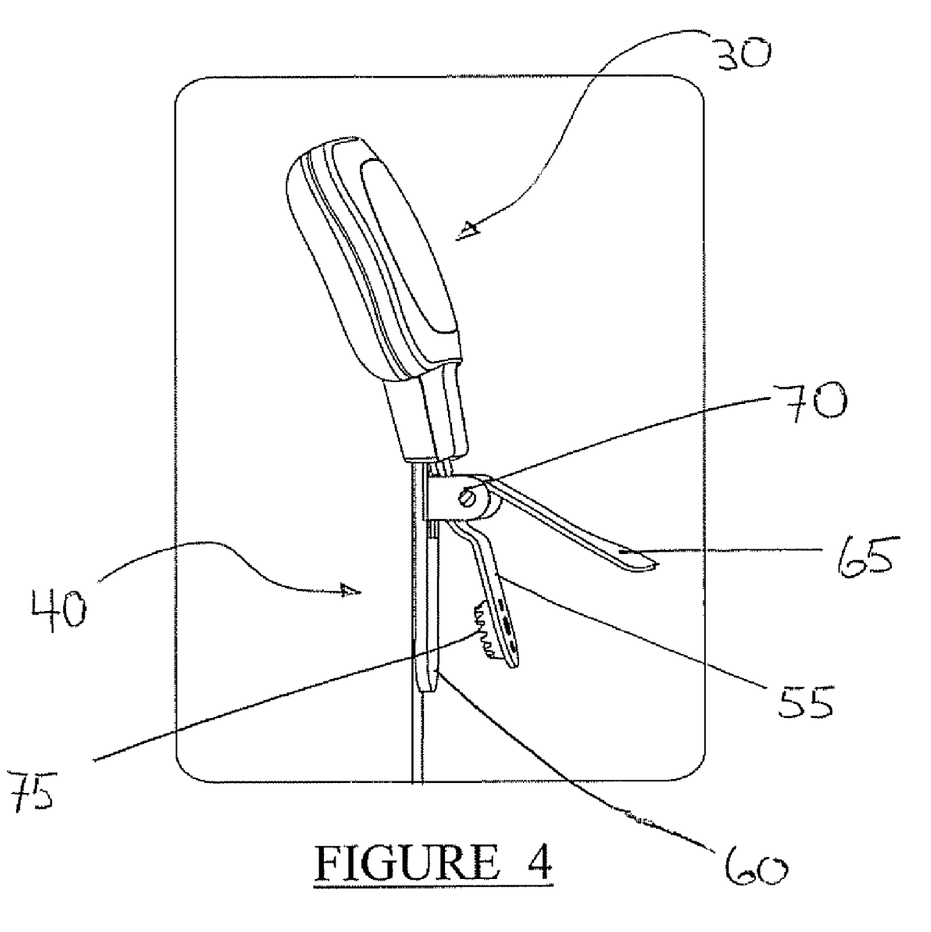
FIG. 4 is a perspective side view of the communication unit and the clamp associated therewith, the clamp disposed in an open position.
Figure 5:
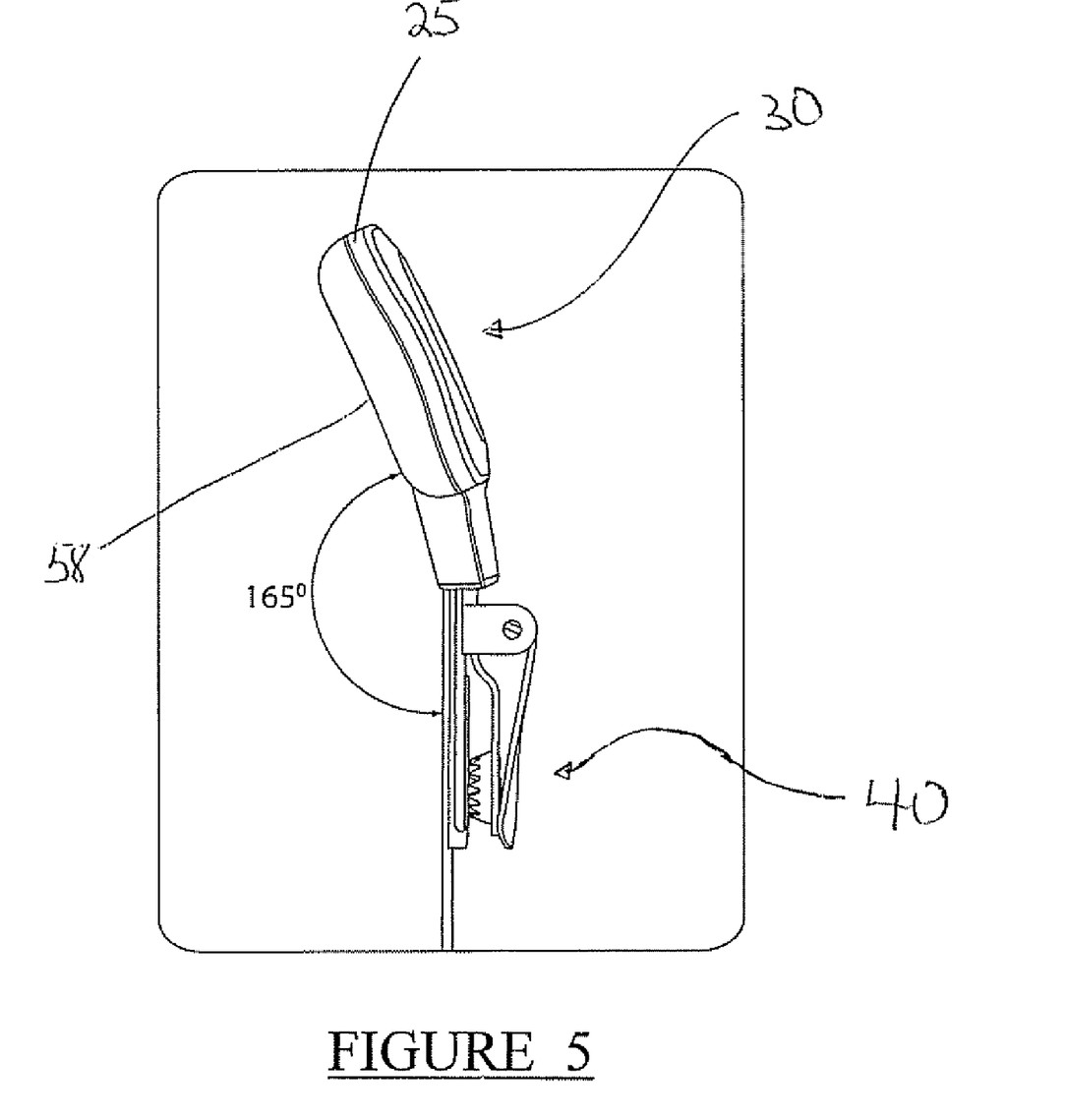
FIG. 5 is another perspective side view of the communication unit and the clamp associated therewith, the clamp disposed in a closed position.

Referring now to FIGS. 4 and 5, clamp unit 40 is designed for facile and fully reversible attachment and disattachment of communication unit 30 to the rim of a shoe, such that even a hemiplegic patient can perform these functions using a single hand.

Clamp unit 40 includes an external (i.e., distal to the shoe) arm or jaw 55, an internal arm or jaw 60 and a locking lever 65 having a fulcrum 70 for closing and locking together jaws 55 and 60. Preferably, when clamp unit 40 is in an open position, jaws 55 and 60 are positioned in a pre-defined angle. The magnitude of this angle is important, since it determines the opening range of the clamp, to fit shoe rims of varying width.

Preferably, arm 55 includes a spring adapted such that clamp unit 40 is in a normally open condition.

Preferably, clamp unit 40 is further adapted such that when clamp unit 40 is in the closed position, with no article clamped between jaws 55 and 60, a small gap (typically less than or equal to one millimeter) exists between jaws 55 and 60. This eliminates the need to apply a strong force in opening clamp unit 40.

Teeth 75, disposed on at least one of jaws 55 and 60, ensure a firm grip of clamp unit 40 on the shoe rim, such that clamp unit 40 is inherently adaptable to a wide range of rim thicknesses, contours, and textures. Locking lever 65 serves to fix jaws 55 and 60 to the rim of the shoe.

Internal jaw 60 has a thin profile, such that when disposed inside shoe 50 of the user, internal jaw 60 does not to protrude into the skin of the foot and cause discomfort to the user.

Typically, clamp unit 40 is permanently and rigidly associated with communication unit 30. The connection of clamp unit 40 to communication unit 30 is achieved by an element (not shown) that, from clamp unit 40, extends into communication unit 30 and is secured therein.

It must be emphasized that other embodiments of clamps and fastening units will be apparent to those skilled in the art. For example, the clamp could have fixed arms that grip the shoe rim by a constant spring force, without an opening and closing mechanism.

As used herein in the specification and in the claims section that follows, the tern "casing", with respect to the electronic communication unit, refers to the at least semi-rigid casing enveloping at least a portion of the electronic communication unit.

As used herein in the specification and in the claims section that follows, the term "housing" and the like, with respect to the electronic communication unit, is meant to include any rigid or semi-rigid projections of the housing, and is meant to include any elements that are at least semi-rigidly attached to the casing. The tern "housing" is specifically meant to include rigid and semi-rigid spines attached to the electronic communication unit, such as the element disclosed in U.S. Design Pat. No. D494,273 to Haugland, et al.

Figure 6A:
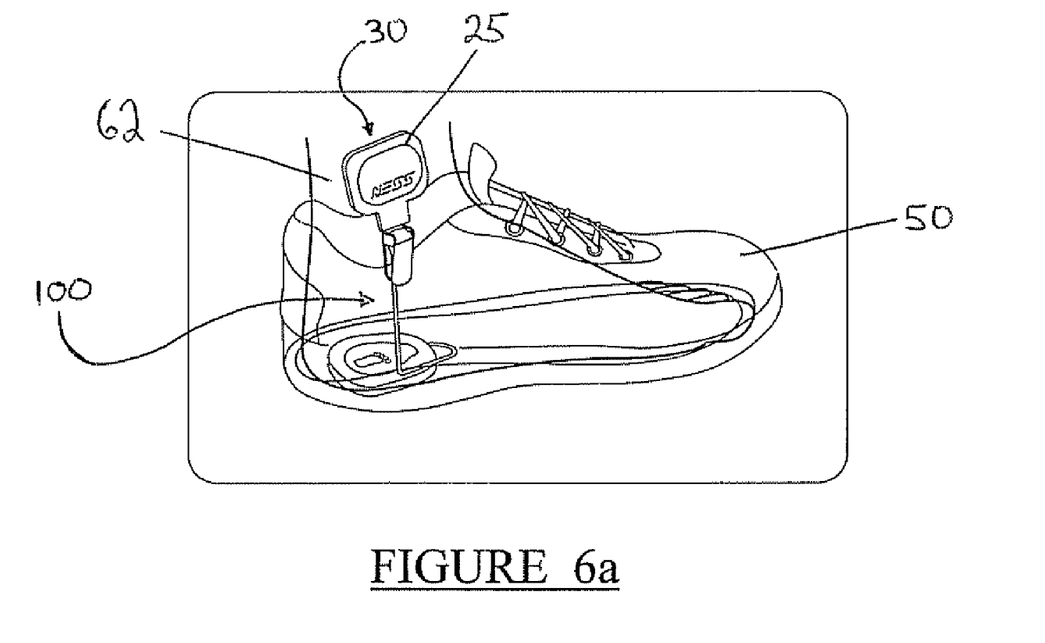
FIG. 6a is a schematic, three-dimensional view of the inventive foot sensor device mounted on the shoe rim, with the communication head hugging the inner calf of the user.
Figure 6B:
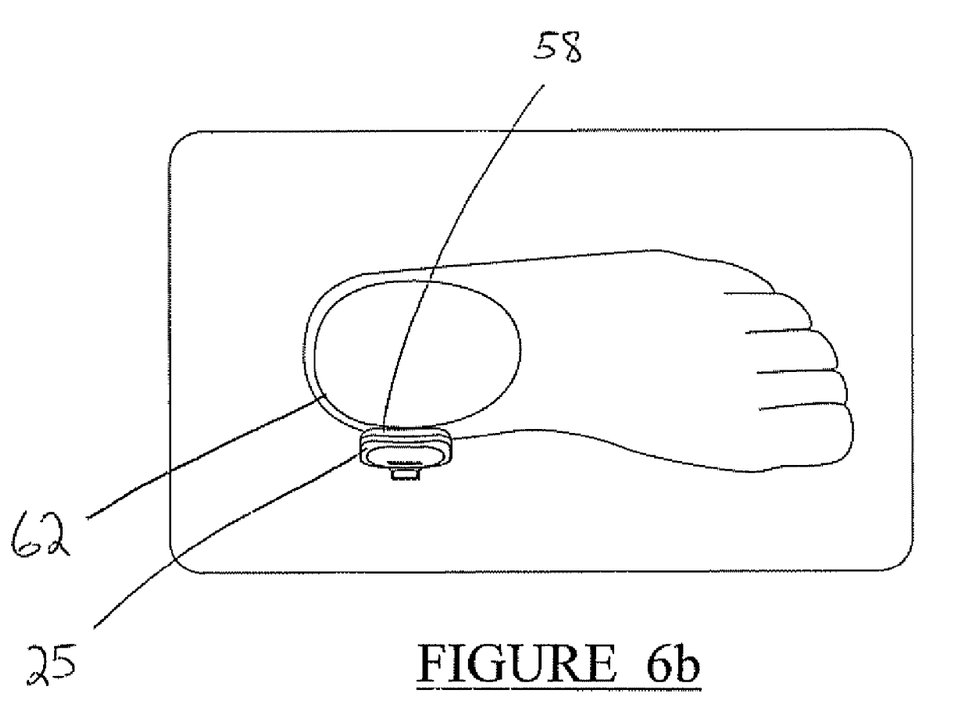

As used herein in the specification and in the claims section that follows, the term "shoe" is meant to include boots, slippers, sandals having an at least semi-rigid position for fastening the fastening unit. Typically, this at least semi-rigid position is the rim of the shoe. Preferably, the shoe has rigid or at least semi-rigid sole and a covering for firmly containing a foot therein FIG. 6a is a schematic, three-dimensional view of the inventive foot sensor device 100 mounted on shoe 50. FIG. 6b is a schematic, three-dimensional top view of FIG. 6a These figures collectively show an inner face 58 of housing 25 (of communication unit 30) hugging an inner calf 62 of the user. The surface of the casing has a small, predetermined curvature that is designed to match and hug the natural curvature of the leg, thereby improving comfort and preventing chafing of communication unit 30 against the skin.

Flexibility, or a degree of freedom, with respect to the leg, is imparted to communication unit 30 by the flexibility of the shoe rim.

Alternatively, communication unit 30 may be corrected to clamp 40 by means of an elastomeric hinge to allow extra flexibility of the casing of communication unit 30 against the foot. The electronic casing may also include a hinge that allows calibrating the angle of the electronic casing against the foot for personal adjustment with respect to specific users and specific shoe dimensions.

Referring back to FIG. 5, the inner facing 58 of housing 25 and clamp unit 40 (internal arm 60) form an angle of about 165°. After extensive tests were performed on users having widely varying physical characteristics, the inventors discovered that within a narrow range of angles, chafing and pressure of housing 25 against the leg of the user is substantially insignificant. In addition, within this narrow range of angles, housing 25 does not protrude away from the leg in an unreasonable fashion, such that housing 25 is protected from bumping into, or being caught by objects during gait. We have found this narrow range of angles to be between 150° and 175°. More preferably the range of angles is between 155° to 160° and 175°, and most preferably, the range is between 160° and 170°.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A foot senor device for gait enhancement, comprising:
   (a) a sensor configured to be disposed within a shoe, the shoe including and upper portion defining a cavity, the shoe further including a rim defining an opening adjacent the cavity, said sensor configured to sense a parameter associated with a gait event;
   (b) an electronic communication unit electrically associated with said sensor, said electronic communication unit adapted to receive a signal pertaining to said parameter, said electronic communication unit having:
      (i) a microcontroller,
      (ii) a transmitter configured to wirelessly transmit gait information based on said signal to a unit of and orthosis distinct from the foot sensor device, and
      (iii) a housing configured to house at least one of said microcontroller and said transmitter, at least a portion of the housing being concave and configured to substantially conform to an adjacent body part when the housing is coupled to the shoe; and
   (c) a fastener attached to said housing, said fastener configured to couple the electronic communication unit to said shoe to secure said electronic communication unit during said gait event, said fastener includes a clamp having at least two arms adapted to fasten around a portion of the rim of said shoe, bottom end of the housing being coupled to a top end of the clamp such that the housing is disposed above the fastener and wholly above the portion of the rim of said shoe when the clamp is fastened around the portion of the rim of said shoe during the gait event, a face of the housing and a face of the clamp forming and angle within a range of about 150° to about 175°.

2. The foot sensor device of claim 1, wherein said is at least semi-rigidly coupled to said housing.

3. The foot sensor device of claim 1, wherein said clamp is rigidly coupled to said housing.

4. The foot sensor device of claim 1, wherein said housing of said electronic communication unit and said sensor are substantially mechanically independent.

5. The foot sensor device of claim 1, wherein said clamp further includes a locking lever adapted to lock said arms in position around said portion of said rim of said shoe.

6. The foot sensor device of claim 1, wherein said face of said housing is generally concave, so as to match a natural curvature of a leg.

7. The foot sensor device of claim 1, wherein said angle is in a range of about 155° to 175°.

8. The foot sensor device of claim 4, wherein said angle is in a range of about 160° to 175°.

9. The foot sensor device of claim 1, wherein said angle is in a range of about 160° to 170°.

10. The foot sensor device of claim 1, wherein said transmitter includes a transceiver.

11. The foot sensor device of claim 1, the device further comprising:
(d) said shoe.

12. The foot sensor device of claim 11, wherein said senor unit is disposed under an insole of said shoe.

13. The foot sensor device of claim 1, wherein of the clamp is configured to be fastened to said shoe using a single hand.

14. A foot senor device for gait enhancement, comprising:
(a) a sensor configured to be disposed within a shoe, the shoe including and upper portion defining a cavity, the shoe further including a rim defining an opening adjacent the cavity, said sensor configured to sense a parameter associated with a gait event;
(b) an electronic communication unit, electrically associated with and physically distinct from said sensor, said electronic communication unit configured to receive a signal associated with said parameter, said electronic communication unit having;
 (i) a microcontroller,
 (ii) a transmitter configured to wirelessly transmit gait information based on said signal to a unit of and orthosis distinct from the foot sensor device, and
 (iii) a housing configured to house at least one of said microcontroller and said transmitter, at least a portion of the housing being concave and configured to substantially conform to an adjacent body part; and
(c) a fastener including a proximal end at least semi-rigidly attached to a distal end of said housing, said fastener adapted to secure said electronic communication unit to said shoe during said gait event, the housing of the electronic communication unit being disposed above the fastener and being disposed wholly above a portion of said rim of said shoe when the electronic communication unit is secured to said shoe by the fastener during the gait event.

15. The foot sensor device of claim 14, wherein said fastener is attachable to said rim of said shoe, said housing disposed at a substantially fixed distance above said portion of said rim, irrespective of a height of said shoe, when said fastener is attached to said rim of said shoe.

16. The foot sensor device of claim 14, wherein said fastener includes a clamp having at least two arms adapted to fasten about a portion of said rim of said shoe.

17. The foot sensor device of claim 14, wherein said fastener is rigidly fixed with respect to the housing such that an angle formed between a face of the housing and a face of the fastener is substantially constant irrespective of a movement of the shoe during said gait event.

18. The foot sensor device of claim 16, wherein said housing and said clamp are coupled to form angle with a range of about 150° to 175° between a face of said housing and a face of said clamp.

19. The foot senor device of claim 16, wherein said clamp is at least Semi-rigidly associated with said housing.

20. A foot sensor device for gait enhancement, comprising:
(a) a sensor having a casing, configured to be disposed within a shoe, the shoe including an upper portion defining a cavity, the shoe further including a rim defining an opening adjacent the cavity, said sensor configured to sense a parameter associated with a gait event;
(b) an electronic communication unit, electrically associated with said sensor, the electronic communication unit configured to receive a signal associated with said parameter, said electronic communication unit having:
 (i) a microcontroller,
 (ii) a transmitter configured to wirelessly transmit gait information based on said signal to a unit of an orthosis distinct from the sensor, and
 (iii) a housing configured to house at least one of said microcontroller and said transmitter, the housing of the electronic communication unit and the casing of the sensor being physically distinct, at least a portion of the housing being concave and configured to substantially conform to an adjacent body part when coupled to the shoe; and
(c) a fastener including a proximal end at least semi-rigidly attached to a distal end of said housing, said fastener adapted to couple the electronic communication unit to a portion of said rim of said shoe during the gait event, the housing of the electronic communication unit being disposed above the fastener and wholly above the portion of said rim when the electronic communication unit is coupled to the portion of said rim of said shoe during the gait event.

21. The foot sensor device of claim 20, wherein when said fastener is coupled to portion of said rim, said housing is disposed at a substantially fixed distance above the portion of said rim, irrespective of a height of said shoe.

22. The foot sensor device of claim 20, wherein said fastener includes a clamp having at least two arms adapted to fasten around the portion of said rim.

23. The foot sensor device of claim 22, wherein said housing of said clamp are attached to form an angle within a range of about 150° to 175° between a face of said housing and a face of said clamp.

24. The foot sensor device of claim 22, wherein said clamp is at least semi-rigidly associated with said housing.

* * * * *

UNITED STATES PATENT AND TRADEMARK OFFICE
CERTIFICATE OF CORRECTION

PATENT NO. : 7,632,239 B2
APPLICATION NO. : 11/552997
DATED : December 15, 2009
INVENTOR(S) : Amit Dar et al.

It is certified that error appears in the above-identified patent and that said Letters Patent is hereby corrected as shown below:

Column 1, line 27, replace "system" with -- system. --.

Column 1, line 33, replace "consuming" with -- consuming. --.

Column 1, line 35, replace "Generally" with -- generally --.

Column 1, line 36, replace "patients" with -- patients. --.

Column 1, line 39, replace "gait" with -- gait. --.

Column 1, line 55, replace "wires" with -- wires. --.

Column 1, line 61, replace "device" with -- device. --.

Column 2, line 7, replace "foot" with -- foot. --.

Column 2, line 13, replace "routine" with -- routine. --.

Column 2, line 17, replace "heel" with -- heel. --.

Column 2, line 39, replace "fashion," with -- fashion. --.

Column 2, line 48, replace "sensing," with -- sensing --.

Column 3, line 61, replace "fastening," with -- fastening --.

Column 5, line 2, replace "drawings" with -- drawings. --.

Column 5, line 4, replace "ways" with -- ways. --.

Column 5, line 48, replace "Casino" with -- Casing --.

Column 5, line 67, replace "moisture" with -- moisture. --.

Column 6, line 25, replace "enhancement" with -- enhancement. --.

Column 6, line 31, replace "wiring 20" with -- wiring 20. --.

Column 7, line 24, replace "tern" with -- term --.

Column 7, line 33, replace "tern" with -- term --.

Column 7, line 43, replace "therein" with -- therein. --.

Column 7, line 56, replace "corrected" with -- connected --.

Column 8, line 17 (claim 1, line 1), replace "senor" with -- sensor --.

Column 8, line 19 (claim 1, line 3), replace "and" with -- an --.

Column 8, line 29 (claim 1, line 13), replace "and" with -- an --.

Column 8, line 41 (claim 1, line 25), after "said shoe," insert -- a --.

CERTIFICATE OF CORRECTION (continued)
U.S. Pat. No. 7,632,239 B2

Column 8, line 47 (claim 1, line 31), replace "and" with -- an --.

Column 8, line 49 (claim 2, line 1), after "wherein said" insert -- clamp --.

Column 8, line 64 (claim 8, line 1), replace "4" with -- 1 --.

Column 9, line 6 (claim 12, line 1), replace "senor" with -- sensor --.

Column 9, line 10 (claim 14, line 1), replace "senor" with -- sensor --.

Column 9, line 12 (claim 14, line 3), replace "and" with -- an --.

Column 9, line 16 (claim 14, line 7), replace "unit," with -- unit --.

Column 9, line 20 (claim 14, line 11), replace "having;" with -- having: --.

Column 9, line 23 (claim 14, line 14), replace "and" with -- an --.

Column 10, line 2 (claim 18, line 2), after "coupled to form" insert -- an --, and replace "with" with -- within --.

Column 10, line 3 (claim 18, line 3), after "150° to" insert -- about --.

Column 10, line 5 (claim 19, line 1), replace "senor" with -- sensor --.

Column 10, line 6 (claim 19, line 2), replace "Semi" with -- semi --.

Column 10, line 38 (claim 21, line 2), after "coupled to" insert -- the --.

Column 10, line 45 (claim 23, line 2), replace "of" with -- and --.

Column 10, line 46 (claim 23, line 3), after "150° to" insert -- about --.

Signed and Sealed this

Twenty-third Day of March, 2010

David J. Kappos
*Director of the United States Patent and Trademark Office*